United States Patent
Perkins, III

(10) Patent No.: US 6,586,663 B2
(45) Date of Patent: Jul. 1, 2003

(54) MUTANT DWARFISM ALLELE OF CLEOME

(75) Inventor: Ralph Tyler Perkins, III, Gilroy, CA (US)

(73) Assignee: Goldsmith Seeds Inc., Gilroy, CA (US)

( * ) Notice: Subject to any disclaimer, the term of this patent is extended or adjusted under 35 U.S.C. 154(b) by 0 days.

(21) Appl. No.: 09/964,281

(22) Filed: Sep. 26, 2001

(65) Prior Publication Data

US 2003/0093843 A1 May 15, 2003

(51) Int. Cl.$^7$ .............................. A01H 1/00; A01H 5/00; A01H 5/10; C12N 5/04; C12N 15/01
(52) U.S. Cl. .................... 800/323; 435/430.1; 800/266; 800/269
(58) Field of Search ................................. 800/295, 298, 800/260, 266, 268, 269, 270, 323; 435/410, 430, 430.1, 431

(56) References Cited

U.S. PATENT DOCUMENTS 5,523,520 A * 6/1996 Hunsperger et al. ........ 435/410

OTHER PUBLICATIONS

Dodds et al. 1982. Chapter 1, pp 1–9. In: Experiments in plant tissue culture. Cambridge Univ. Press, NY.*
Kers et al. 1970. Studies in cleome. IV. Svensk Botanisk Tidskrift 64(3):263–283.*
Ladd et al. 1984. Genetics of flower color in spider flower. J. Amer. Soc. Hort. Sci 109(6):79–761.*
Kraft et al. 2000. Linkage disequilibrium and fingerprinting in sugar beet. Theor. Appl. Genet. 101:323–326.*
Eshed et al. 1996. Less–than–additive epistatic interactions of quantitative trait loci in tomato. Genetics 143:1807–1817.*
Ladd et al. 1984. Genetics of flower color in spider flower. J. Amer. Soc. Hort. Sci 109(6):79–761.*

* cited by examiner

Primary Examiner—David T. Fox
Assistant Examiner—Ashwin Mehta
(74) Attorney, Agent, or Firm—Jondle & Associates PC

(57) ABSTRACT

This present invention relates to a dwarf cleome plant, seed, variety and hybrid. More specifically, the invention relates to a cleome plant having a mutant allele for dwarfism, which results in the reduced plant size. The invention also relates to crossing inbreds, varieties and hybrids containing the dwarf allele to produce novel types and varieties of dwarf cleome plants for ornamental purposes.

8 Claims, No Drawings

MUTANT DWARFISM ALLELE OF CLEOME

FIELD OF THE INVENTION

The present invention relates to a novel dwarfism allele of cleome, which results in a reduction in plant size. This present invention also relates to a cleome seed, a cleome plant, a cleome variety and a cleome hybrid, which contain the dwarfism allele. In addition, the present invention is directed to transferring the dwarfism allele in the cleome plant to other cleome varieties and species and is useful for producing novel types and varieties of dwarf cleome.

BACKGROUND OF THE INVENTION

Cleome of the family Capparidaceae, is composed of approximately 200 species of annual or perennial herbs and sub shrubs. One annual species, *Cleome hasslerana*, has been cultivated as a garden and border plant. Only a few varieties of cleome are available commercially, including 'Helen Campbell', 'White Queen', 'Pink Queen', 'Rose Queen', 'Cherry Queen' and 'Violet Queen'. With the exception of flower color, these varieties are very similar in appearance and performance, growing as frost-tender annuals to a height of approximately five feet. To date, no other plant form of *Cleome hasslerana* has been available and there is no known dwarfism in any cultivars of Cleome. A dwarf form of cleome would be particularly desirable to the commercial greenhouse trade as well as to commercial landscape and home gardeners.

SUMMARY OF THE INVENTION

The present invention relates to a cleome seed, a cleome plant, a cleome variety, a cleome hybrid, and a method for producing a cleome plant.

More specifically, the invention relates to a dwarfism allele, which produces a cleome plant that is reduced in size.

In one aspect of the invention, under greenhouse production, the dwarf cleome of the present invention can be grown in a smaller container and under a higher bench density than the standard form. In another aspect the dwarf cleome of the present invention can be shipped in flower at a much reduced height and size, allowing higher shipping density and reduced cost per unit. Shipping and sale in flower increases unit value. In another aspect of this invention the dwarf cleome translates into higher display density and greater visual appeal, increasing per unit value for the retailer. The consumer is offered a novel and more appealing product at the point of sale, which is more easily transported and has a wider utility in the home landscape. In the garden, the dwarf form of the present invention, with it's compact growth habit and compressed flower canopy, offers a plant with a broader range of uses and greater color impact.

The genetic factor of the present invention which is capable of transmitting the plant size reduction has been determined to be a mutant single recessive allele, which has been designated "H35". It is a feature of the present invention that this single mutant allele H35 may be used in and transferred to different cleome varieties and to other cleome species.

The present invention further relates to a method of producing the disclosed cleome plants and seeds by crossing a dwarf cleome plant of the instant invention with another cleome plant. The invention also relates to the transfer of the genetic dwarfism into other cleome plants.

DETAILED DESCRIPTION OF THE INVENTION

In order to provide an understanding of the terms used in the specification and claims, the following definitions are provided:

Dwarf, dwarfism—means a plant possessing shortened internodes and reduced foliage size, resulting in a smaller than normal plant form.

Compact growth habit—means plants that are smaller than normal as a result of shortened internodes.

Mature—means 5-month-old field grown plants derived from transplanted plantlets. The plantlets are grown from seed in the greenhouse for approximately 6 weeks prior to being transplanted.

Mature plant height—means the measurement in inches from the soil line to the uppermost tip of the plant. Mature plant height data was taken on 5-month-old field grown plants.

Mature plant width—means the measurement in inches at the broadest point of the plant. Data was taken on 5-month-old field grown plants.

Leaf length—means the distance in inches between the base of the petiole and the tip of the primary leaflet. Leaf samples were taken from two nodes below the first flower on 5-month-old field grown plants.

Leaf width index—means the sum of the length in inches of the two leaflets adjacent to the primary leaflet. Leaf samples were taken from two nodes below the first flower on 5-month-old field grown plants.

Plant height at first flower—means the total height of the plant in inches from the soil line to the first fully opened flower. Data was taken on field grown plants.

Field conditions—means plants grown to maturity in an open field. Seeds are sown in the greenhouse and grown for approximately 6 weeks to produce plantlets. These plantlets are then transplanted to the field on or about the average last day of frost for the specific field location.

The present invention relates to a novel plant-dwarfing allele in the genus Cleome that is phenotypically expressed in the reduction in plant size. As the term is used herein, dwarf and dwarfism refer to a condition where in the plant and all its parts are reduced in size by a substantial amount. Additionally, the plant parts, being smaller, have a finer texture and a more delicate appearance than those of standard cleome.

This present invention is directed to developing unique plants of the cleome species. The cleome of the present invention expresses a substantial reduction in plant size. A transferable gene or allele that conveys this dwarf characteristic has been isolated and incorporated into other genetic backgrounds. The dwarf allele of the instant invention has also been expressed in different genetic backgrounds of cleome. The present invention results in a mature plant height reduction of about 30% to about 50%, plant width reduction of about 20% to about 40%, and reduction of plant height at first flower of about 40% to about 60%, depending on the genetic background as shown in Tables 1–3. To date, except for the present invention, there is no known dwarfism in any cultivars of Cleome.

It is standard practice in the industry to treat young plants several times with chemical plant growth regulators (PGR) such as B-9 (Alar), Cycocel or Bonzi to reduce internode length to obtain shorter, more compact plants. While this effect may appear somewhat similar to that of the dwarfing allele, it is important to note that this effect is temporary and the plants will achieve their full height potential when planted out in the field and grown full season. Genetic dwarf lines will also develop proportionately shorter and more compact plants following treatment with PGRs, resulting in plants even smaller than the same PGR-treated commercial varieties.

As used herein, the term plant includes plant cells, plant protoplasts, plant cell tissue cultures from which cleome plants can be regenerated, plant calli, plant clumps and plant cells that are intact in plants or parts of plants, such as embryos, pollen, ovules, flowers, stems, leaves, roots, root tips, anthers, and the like.

EXAMPLES

The following examples are provided to further illustrate the present invention and are not intended to limit the invention beyond the limitations set forth in the appended claims.

Example 1

Development of Mutant Dwarfism Allele H35

This previously unknown dwarfism characteristic arose from an induced mutation project for the specific purpose of generating dwarf-breeding material. On Feb. 12, 1992, commercial seeds of 'Rose Queen' were treated with the chemical mutagen nitroso-methyl urea (NMU). Following treatment, the seeds were sown under controlled greenhouse conditions and subsequently transplanted to a greenhouse.

In the first generation ($M_1$), the seedlings exhibited typical symptoms of mutation treatment: high percentages of seed mortality, retarded growth, yellowing,,and distorted growth. Seed was gathered from $M_1$ generation plants having the most visible phenotypic indications of mutagen effects. The subsequent $M_2$ yielded twelve shorter individuals. Collateral residual effects of the original mutations (sterility and reduced fertility, chlorotic sectors, albinism, distorted growth and instability) prevented most of these lines from being advanced. One line, CM8: F15-2, was stable for dwarfism and contained the H35 allele of the present invention. Selections out of breeding crosses with CM8: F15-2 and their subsequent back crosses created the foundation for the dwarf cleome-breeding program.

The dwarf phenotype of the present invention generally segregates as a simple recessive allele, yielding on average a 1 dwarf to 3 tall $F_2$ segregation ratio from a (dwarf×tall) cross, and 1 dwarf to 1 tall ratio from a (dwarf×tall)×dwarf backcross. The degree of dwarfing varies slightly between different backgrounds as shown in Tables 1–5. The degree of dwarfing is also affected by heterosis as shown in the data of the inbreds vs. hybrids, in Tables 1–5.

Example 2

Dwarf Inbred Lines Developed Containing Mutant Dwarfism Allele H35

The mutant allele H35 has been backcrossed into several different genetic backgrounds to produce a number of different inbreds including inbreds 146-8, 159-12 and 169-2 which are described below.

Blush inbred CM8: F15-2 has a pedigree of:

H35-1-1-2-2 (also called H35)

A sample of 'Rose Queen' was mutated, selections were self-pollinated, a dwarf individual H35 was selected and selfed 3 additional generations. This was the original source of all subsequent dwarf lines having the H35 allele.

Dwarf roseinbred 146-8 was derived from the following pedigree:

[H35×(CoRed×H.25)]-1-1-2-(8)

Original dwarf H35 was crossed with a tall rose inbred. The dwarf trait was recovered in the F2 generation, selfed 1 additional generation, and then mass selected to improve other horticultural traits.

Dwarf lavender inbred 159-12 was derived from the pedigree:

[(H35×H2.5)×H35]-2-1-1L-(8)-(12)

Original dwarf H35 was crossed with a tall lavender inbred and then backcrossed to the dwarf. The dwarf trait was recovered in the F2 generation and then selfed once and mass selected 2 additional generations to improve other horticultural traits.

Dwarf purple inbred 169-2 was derived from the pedigree:

{[(400×H35)×H2.5]-1}×H35-1-2

Original dwarf H35 was crossed with a tall purple inbred and then crossed again to another purple inbred. This cross was selfed once and backcrossed to the dwarf and then selfed 2 additional generations to improve other horticultural traits.

Example 3

Dwarf Hybrids Developed Containing Mutant Allele H35

The mutant allele H35 has been crossed into a number of different genetic backgrounds including the following hybrids:

White hybrid 4000-1 has the pedigree:

102-9×107-10=[H35×(H35×L1.5)]-5-1-2-1-(6)-(9)× [RQ×H35)×(H35×L1.5)]-3-1-(4)-(10)

A testcross hybrid between two true-breeding dwarf inbreds.

Blush hybrid 4000-2 has the pedigree:

111-6×117-22={[(RQ×H2.5)×H35]×(H35×L1.5)}-1-1-(2)-(6)×H35-1-1-2-2-3-2L-(8)-(22)

A testcross hybrid between two true-breeding dwarf inbreds.

Rose hybrid 4000-4 has the pedigree:

146-8×149-8={H35×(CoRed-H2.5)]-1-1-2-(8)×{ [(CoRed×H2.5)×(400×H35)]×H35}-3-1-3-(8)

A testcross hybrid between two true-breeding dwarf inbreds.

Lavender hybrid 4000-5 has the pedigree:

149-8×159-12={[(CoRed×H2.5)×(400×H35)]×H35}-3-1-3-(8)×[(H35×H2.5)×H35]-2-1-1L-(8)-(12)

A testcross hybrid between two true-breeding dwarf inbreds.

Example 4

Effect of Dwarf Allele on Mature Plant Height, Width, and Height at First Flower of Dwarf Inbred Lines (146-8, 159-12 and 169-2) and Dwarf Hybrids (4000-1, 4000-2, 4000-4, and 4000-5) as Compared to Commercial Variety 'Rose Queen' (RQ)

As shown in Tables 1–3, inbred lines derived from breeding crosses between CM8:15-2 and different color backgrounds are represented in these tables by 146-8,159-12 and 169-2. Hybrids between these and similar dwarf lines are represented in Tables 1-5 by 4000-1 White, 4000-2

Blush, 4000-4 Rose and 4000-5 Lavender. 'Rose Queen' (RQ) is the full-sized commercial comparison.

Field measurements were taken for plant height, width, and height at first flower at maturity. Measurements were made on ten random samples taken from populations of the above lines.

Heights of the dwarf inbred lines ranged from 50–54% of the commercial variety 'Rose Queen'. Heights of the dwarf hybrids ranged from 61–69% of the commercial variety 'Rose Queen' as shown in Table 1.

Widths of the dwarf inbred lines ranged from 59–66% of the commercial variety 'Rose Queen'. Widths of the dwarf hybrid lines ranged from 73–80% of the commercial variety 'Rose Queen' as shown in Table 2.

Height at first flower of the dwarf inbred lines ranged from 42–46% of the commercial variety 'Rose Queen'. Height at first flower of the dwarf hybrid lines ranged from 49–62% of the commercial variety 'Rose Queen' as shown in Table 3.

Differences in mature plant height and width, and height at first flower between the inbreds and hybrids are the result of heterosis.

Example 5

Effect of Dwarf Allele on Mature Plant Leaf Length and Width of Dwarf Inbred Lines (148-6, 159-12 and 169-2) and Dwarf Hybrids (4000-1, 4000-2, 4000-4, and 4000-5) as Compared to Commercial 'Rose Queen" (RQ)

As shown in Tables 4 and 5, field measurements were taken for leaf length and width on ten random samples from populations of the above lines. Leaf samples were taken from two nodes below the first flower. Leaf length is defined as the distance between the base of the petiole and the tip of the primary leaflet. Leaf width index is defined as the sum of the lengths of the two leaflets adjacent to the primary leaflet.

Leaf length of the dwarf inbred lines ranged from 61–71% of the commercial variety 'Rose Queen'. Leaf length of the dwarf hybrid lines ranged from 71–78% of the commercial variety 'Rose Queen' as shown in Table 4.

Leaf width index of the dwarf inbred lines ranged from 53–67% of the commercial variety 'Rose Queen'. Leaf width index of the dwarf hybrid lines ranged from 62–68% of the commercial variety 'Rose Queen' as shown in Table 5.

TABLE 1

Cleome t-Tests - Mature Plant Height
t-Test; Two-Sample Assuming Unequal Variances - measurements in inches

|  | RQ | 146-8 | RQ | 159-12 | RQ | 169-2 |
|---|---|---|---|---|---|---|
| Mean | 63.3 | 31.8 | 63.3 | 33.4 | 63.3 | 33.9 |
| Variance | 2.2 | 1.1 | 2.2 | 0.5 | 2.2 | 0.3 |
| Observations | 10 | 10 | 10 | 10 | 10 | 10 |
| Hypothesized Mean Difference | 0 |  | 0 |  | 0 |  |
| df | 16 |  | 13 |  | 12 |  |
| t Stat | 54.83 |  | 57.31 |  | 58.16 |  |
| P(T <= t) two-tail | 1.21E−19 |  | 5.13E−17 |  | 4.41E−16 |  |
| Average Height as a % of RQ |  | 50 |  | 53 |  | 54 |

|  | RQ | 4000-1 | RQ | 4000-2 | RQ | 4000-4 | RQ | 4000-5 |
|---|---|---|---|---|---|---|---|---|
| Mean | 63.3 | 41.2 | 63.3 | 41.8 | 63.3 | 38.4 | 63.3 | 43.4 |
| Variance | 2.2 | 0.8 | 2.2 | 1.3 | 2.2 | 1.4 | 2.2 | 2.7 |
| Observations | 10 | 10 | 10 | 10 | 10 | 10 | 10 | 10 |
| Hypothesized Mean Difference | 0 |  | 0 |  | 0 |  | 0 |  |
| df | 15 |  | 17 |  | 17 |  | 18 |  |
| t Stat | 39.84 |  | 36.23 |  | 41.44 |  | 28.30 |  |
| P(T <= t) two-tail | 1.24E−16 |  | 1.55E−17 |  | 1.62E−18 |  | 2.24E−16 |  |
| Average Height as a % of RQ |  | 65 |  | 65 |  | 61 |  | 69 |

TABLE 2

Cleome t-Tests - Mature Plant Width
t-Test: Two-Sample Assuming Unequal Variances - measurements in inches

|  | RQ | 146-8 | RQ | 159-12 | RQ | 169-2 |
|---|---|---|---|---|---|---|
| Mean | 46.3 | 27.1 | 46.3 | 28.8 | 46.3 | 30.4 |
| Variance | 37.3 | 1.2 | 37.3 | 0.6 | 37.3 | 0.9 |
| Observations | 10 | 10 | 10 | 10 | 10 | 10 |
| Hypothesized Mean Difference | 0 |  | 0 |  | 0 |  |
| df | 10 |  | 9 |  | 9 |  |
| t Stat | 9.78 |  | 8.98 |  | 8.13 |  |
| P(T <= t) two-tail | 1.95E−06 |  | 8.68E−06 |  | 1.95E−05 |  |
| Average Width as a % of RQ |  | 59 |  | 62 |  | 66 |

|  | RQ | 4000-1 | RQ | 4000-2 | RQ | 4000-4 | RQ | 4000-5 |
|---|---|---|---|---|---|---|---|---|
| Mean | 46.3 | 33.7 | 46.3 | 35.1 | 46.3 | 33.6 | 46.3 | 37.1 |
| Variance | 37.3 | 0.9 | 37.3 | 1.4 | 37.3 | 3.2 | 37.3 | 3.2 |
| Observations | 10 | 10 | 10 | 10 | 10 | 10 | 10 | 10 |
| Hypothesized Mean Difference | 0 |  | 0 |  | 0 |  | 0 |  |

TABLE 2-continued

Cleome t-Tests - Mature Plant Width
t-Test: Two-Sample Assuming Unequal Variances - measurements in inches

| | | | | |
|---|---|---|---|---|
| df | 9 | 10 | 11 | 11 |
| t Stat | 6.44 | 5.69 | 6.31 | 4.57 |
| P(T <= t) two-tail | 1.19E-04 | 2.02E-04 | 5.75E-05 | 8.06E-04 |
| Average Width as a % of RQ | 73 | 76 | 73 | 80 |

TABLE 3

Cleome t-Tests - Plant Height at 1st Flower
t-Test: Two-Sample Assuming Unequal Variances - measurements in inches

| | RQ | 146-8 | RQ | 159-12 | RQ | 169-2 |
|---|---|---|---|---|---|---|
| Mean | 31.7 | 13.4 | 31.7 | 13.5 | 31.7 | 14.5 |
| Variance | 11.8 | 0.7 | 11.8 | 0.9 | 11.8 | 0.7 |
| Observations | 10 | 10 | 10 | 10 | 10 | 10 |
| Hypothesized Mean Difference | 0 | | 0 | | 0 | |
| df | 10 | | 10 | | 10 | |
| t Stat | 16.37 | | 16.13 | | 15.38 | |
| P(T <= t) two-tail | 1.51E-08 | | 1.74E-08 | | 2.75E-08 | |
| Average Height at 1$^{st}$ Flower as a % of RQ | | 42 | | 43 | | 46 |

| | RQ | 4000-1 | RQ | 4000-2 | RQ | 4000-4 | RQ | 4000-5 |
|---|---|---|---|---|---|---|---|---|
| Mean | 31.7 | 18 | 31.7 | 19.8 | 31.7 | 15.6 | 31.7 | 18.5 |
| Variance | 11.8 | 0.7 | 11.8 | 1.3 | 11.8 | 0.5 | 11.8 | 0.9 |
| Observations | 10 | 10 | 10 | 10 | 10 | 10 | 10 | 10 |
| Hypothesized Mean Difference | 0 | | 0 | | 0 | | 0 | |
| Df | 10 | | 11 | | 10 | | 10 | |
| t Stat | 1228 | | 10.41 | | 14.53 | | 11.70 | |
| P(T <= t) two-tail | 2.36E-07 | | 4.96E-07 | | 4.75E-08 | | 3.71E-07 | |
| Average Height at 1st Flower as a % of RQ | | 57 | | 62 | | 49 | | 58 |

TABLE 4

Cleome t-Tests - Leaf Length
t-Test: Two-Sample Assuming Unequal Variances - measurements in inches

| | RQ | 146-8 | RQ | 159-12 | RQ | 169-2 |
|---|---|---|---|---|---|---|
| Mean | 5.9 | 4.2 | 5.9 | 3.9 | 5.9 | 3.6 |
| Variance | 0.3 | 0.1 | 0.3 | 0.1 | 0.3 | 0.1 |
| Observations | 10 | 10 | 10 | 10 | 10 | 10 |
| Hypothesized Mean Difference | 0 | | 0 | | 0 | |
| Df | 17 | | 15 | | 16 | |
| t Stat | 8.57 | | 10.46 | | 11.73 | |
| P(T <= t) two-tail | 1.42E-07 | | 2.76E-08 | | 2.86E-09 | |
| Average Leaf Length as a % of RQ | | 71 | | 66 | | 61 |

| | RQ | 4000-1 | RQ | 4000-2 | RQ | 4000-4 | RQ | 4000-5 |
|---|---|---|---|---|---|---|---|---|
| Mean | 5.9 | 4.2 | 5.9 | 4.2 | 5.9 | 4.4 | 5.9 | 4.6 |
| Variance | 0.3 | 0.1 | 0.3 | 0.2 | 0.3 | 0.1 | 0.3 | 0.2 |
| Observations | 10 | 10 | 10 | 10 | 10 | 10 | 10 | 10 |
| Hypothesized Mean Difference | 0 | | 0 | | 0 | | 0 | |
| Df | 17 | | 18 | | 13 | | 17 | |
| t Stat | 8.30 | | 7.90 | | 8.40 | | 6.27 | |
| P(T <= t) two-tail | 2.20E-07 | | 2.91E-07 | | 1.30E-06 | | 8.42E-06 | |
| Average Leaf Length as a % of RQ | | 71 | | 71 | | 75 | | 78 |

TABLE 5

Cleome t-Tests - Leaf Width Index
t-Test: Two-Sample Assuming Unequal Variances- -measurements in inches

|  | RQ | 146-8 | RQ | 159-12 | RQ | 169-2 |
|---|---|---|---|---|---|---|
| Mean | 6.0 | 4.0 | 6.0 | 3.3 | 6.0 | 3.2 |
| Variance | 0.3 | 0.1 | 0.3 | 0.1 | 0.3 | 0.0 |
| Observations | 10 | 10 | 10 | 10 | 10 | 10 |
| Hypothesized Mean Difference | 0 |  | 0 |  | 0 |  |
| df | 14 |  | 13 |  | 10 |  |
| t Stat | 10.05 |  | 13.76 |  | 15.45 |  |
| P(T <= t) two-tail | 8.79E−08 |  | 3.98E−09 |  | 2.63E−08 |  |
| Average Leaf Width as a % of RQ |  | 67 |  | 55 |  | 53 |

|  | RQ | 4000-1 | RQ | 4000-2 | RQ | 4000-4 | RQ | 4000-5 |
|---|---|---|---|---|---|---|---|---|
| Mean | 6.0 | 3.9 | 6.0 | 3.7 | 6.0 | 3.9 | 6.0 | 4.1 |
| Variance | 0.3 | 0.0 | 0.3 | 0.0 | 0.3 | 0.0 | 0.3 | 0.0 |
| Observations | 10 | 10 | 10 | 10 | 10 | 10 | 10 | 10 |
| Hypothesized Mean Difference | 0 |  | 0 |  | 0 |  | 0 |  |
| df | 11 |  | 9 |  | 12 |  | 10 |  |
| t Stat | 11.25 |  | 12.85 |  | 11.21 |  | 10.18 |  |
| P(T <= t) two-tail | 2.25E−07 |  | 4.29E−07 |  | 1.03E−07 |  | 1.35E−06 |  |
| Average Leaf Width as a % of RQ |  | 65 |  | 62 |  | 65 |  | 68 |

Example 6

Demonstration of the Relative Uniformity in Height, Width and Height to 1st Flower in 'Rose Queen' (RQ), 'White Queen' (WQ) and 'Violet Queen' (VQ)

Field measurements were taken for plant height, width, and height at first flower at maturity. Measurements were made on ten random samples taken from populations of the above lines as shown in Tables 6–8.

TABLE 6

Cleome t-Tests-Height of commercial Varieties
t-Test: Two-Sample Assuming Unequal Variances- -measurements in inches

|  | RQ | WQ | RQ | VQ |
|---|---|---|---|---|
| Mean | 63.3 | 63.4 | 63.3 | 67.5 |
| Variance | 2.2333 | 4.7111 | 2.2333 | 21.3889 |
| Observations | 10 | 10 | 10 | 10 |
| Hypothesized Mean Difference | 0 |  | 0 |  |
| df | 16 |  | 11 |  |
| t Stat | −0.12 |  | −2.7327 |  |
| P(T <= t) two-tail | 0.9060 |  | 0.0195 |  |

TABLE 7

Cleome t-Tests-Width of Commercial Varieties
t-Test: Two-Sample Assuming Unequal Variances- -measurements in inches

|  | RQ | WQ | RQ | VQ |
|---|---|---|---|---|
| Mean | 46.3 | 46 | 46.3 | 52.2 |
| Variance | 37.3444 | 31.7778 | 37.3444 | 69.0667 |
| Observations | 10 | 10 | 10 | 10 |
| Hypothesized Mean Difference | 0 |  | 0 |  |
| df | 18 |  | 17 |  |
| t Stat | 0.1141 |  | −1.8087 |  |
| P(T <= t) two-tail | 0.9104 |  | 0.0882 |  |

TABLE 8

Cleome t-Tests-Height to 1st Flower of Commercial Varieties
t-Test: Two-Sample Assuming Unequal Variances- -measurements in inches

|  | RQ | WQ | RQ | VQ |
|---|---|---|---|---|
| Mean | 31.7 | 29.9 | 31.7 | 32.7 |
| Variance | 11.7889 | 11.8778 | 11.7889 | 6.6778 |
| Observations | 10 | 10 | 10 | 10 |
| Hypothesized Mean Difference | 0 |  | 0 |  |
| Df | 18 |  | 18 |  |
| T Stat | 1.1700 |  | 1.1700 |  |
| P(T <= t) two-tail | 0.2572 |  | 0.2572 |  |

DEPOSIT INFORMATION

*Cleome hasslerana* seeds containing the H35 mutant allele have been placed on deposit with the American Type Culture Collection (ATCC), 10801 University Boulevard, Manassas, Va. 20110-2209 on Sep. 25, 2001 and having Deposit Accession Number PTA-3724.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A *Cleome hasslerana* seed comprising a recessive allele for dwarfism designated H35, wherein a sample of said seed has been deposited under ATCC Accession No. PTA-3724.

2. A dwarf cleome plant produced by growing the seed of claim 1.

3. The cleome plant of claim 2, wherein said plant has a compact growth habit.

4. Pollen of the plant of claim 2.

5. An ovule of the plant of claim 2.

6. A method for producing F1 hybrid *Cleome hasslerana* seed comprising crossing a first parent *Cleome hasslerana* plant with a second parent *Cleome hasslerana* plant and harvesting the resultant F1 hybrid *Cleome hasslerana* seed, wherein first or second parent *Cleome hasslerana* plant is the *Cleome hasslerana* plant of claim 2 and wherein said F1 hybrid *Cleome hasslerana* plant comprises an allele for dwarfism designated H35.

7. A first generation (F1) hybrid cleome plant produced by growing said hybrid cleome seed produced from the method of claim 6, wherein said F1 cleome plant contains a recessive allele for dwarfism designated H35.

8. F2 hybrid seed produced from said hybrid plant of claim 7, wherein said F2 hybrid seed contains said allele for dwarfism designated H35.

* * * * *